United States Patent
Anderson et al.

(10) Patent No.: US 6,428,512 B1
(45) Date of Patent: Aug. 6, 2002

(54) GUIDEWIRE WITH IMPROVED LESION MEASUREMENT

(75) Inventors: David M. Anderson, Temecula; Mark T. Richardson, Escondido, both of CA (US); Gina Eileen Stephens, Tokyo (JP)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 133 days.

(21) Appl. No.: 09/686,143

(22) Filed: Oct. 10, 2000

(51) Int. Cl.$^7$ .............................................. A61M 25/00
(52) U.S. Cl. ................. 604/170.01; 604/529; 600/434; 600/585
(58) Field of Search .......................... 604/117, 170.01, 604/170.02, 529; 600/434, 585

(56) References Cited

U.S. PATENT DOCUMENTS

| | | | |
|---|---|---|---|
| 4,279,252 A | * | 7/1981 | Martin ........................ 600/435 |
| 5,253,653 A | * | 10/1993 | Daigle et al. ............... 600/585 |
| 5,409,004 A | * | 4/1995 | Sloan ......................... 600/434 |
| 5,458,615 A | | 10/1995 | Klem et al. |
| 5,479,938 A | * | 1/1996 | Weier ......................... 600/585 |
| 5,507,768 A | | 4/1996 | Lau et al. |

* cited by examiner

*Primary Examiner*—David J. Walczak
*Assistant Examiner*—Peter deVore
(74) *Attorney, Agent, or Firm*—Fulwider Patton Lee & Utecht, LLP

(57) ABSTRACT

A guidewire having an elongated core having a radiopaque marker on a distal portion of the core and a plurality of indicia on the proximal extremity of the core to facilitate measurement of an intracorporeal location such as a stenotic region within a patient's coronary artery. The guidewire is first positioned within the patient with the distal radiopaque marker at one end of the intracorporeal location and an indicia representing a base reference point is noted on the proximal portion of the guidewire which extends out of the patient. The guidewire is then moved so that the distal radiopaque marker is located at or adjacent to the other end of the intracorporeal location and another indicia on the proximal portion of the guidewire adjacent to the reference point. The distance between the two indicia on the proximal extremity of the guidewire is a measurement of intracorporeal length.

22 Claims, 4 Drawing Sheets

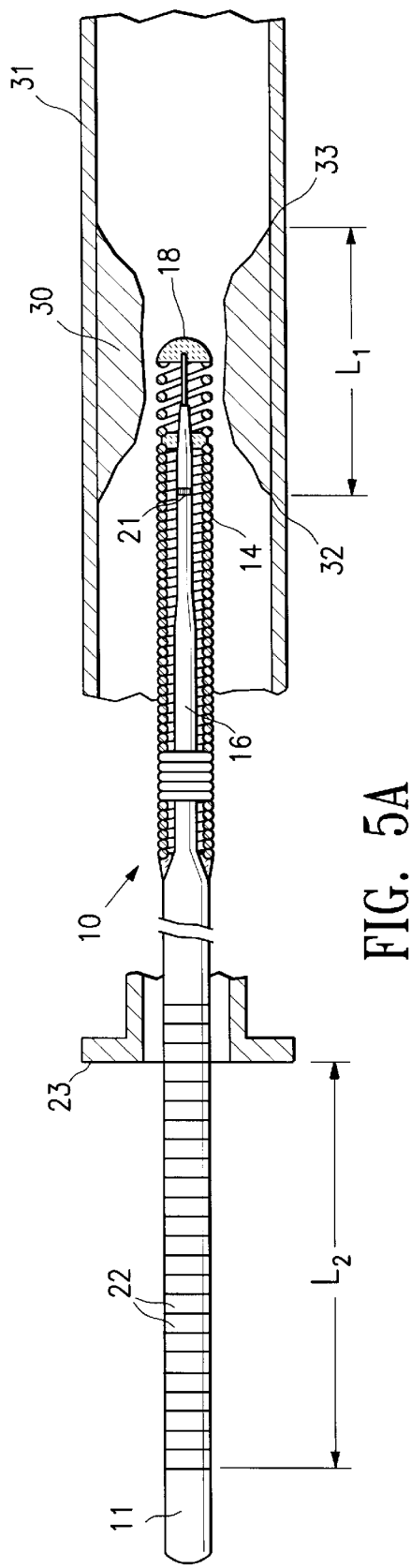
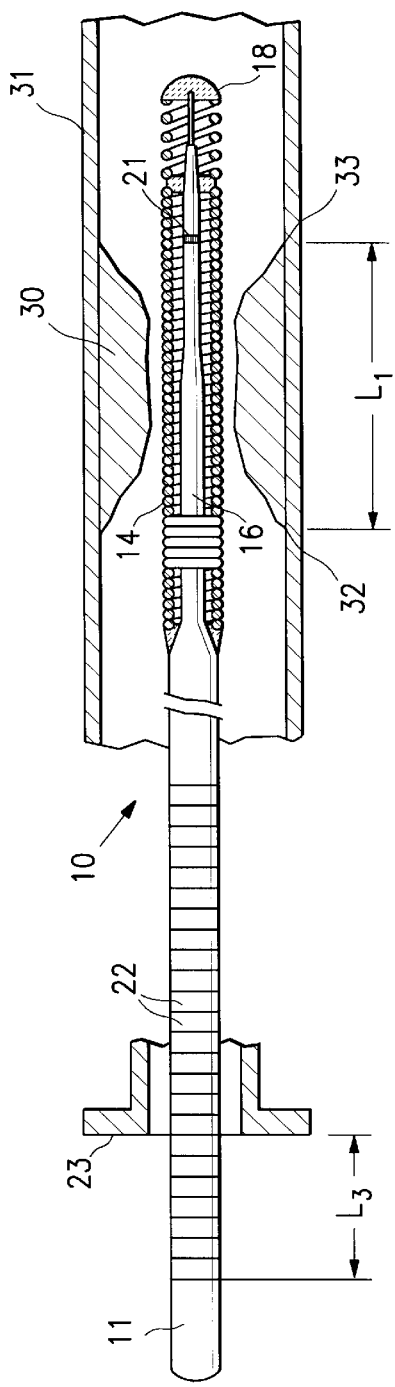
FIG. 5A
FIG. 5B

GUIDEWIRE WITH IMPROVED LESION MEASUREMENT

BACKGROUND OF THE INVENTION

The invention relates to the field of intravascular devices, and particularly to a guidewires suitable for procedures such as angioplasty and/or stent deployment, and the like.

In percutaneous transluminal coronary angioplasty (PTCA) procedures a guiding catheter is first advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

After such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency.

Stents are usually delivered to a desired location within a coronary artery in a contracted condition on a balloon of a catheter, which is very similar in many respects to a balloon angioplasty catheter, and expanded within the patient's artery to a larger diameter by inflating the balloon. After stent deployment, the balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to keep open a stenosed vessel, and strengthen the dilated area by remaining inside the vessel. Instead of first using one catheter to dilate the body lumen and a second catheter to deploy the stent after the dilatation, the stent may be mounted on a balloon catheter and deployed at the same time the balloon is inflated to dilate the stenotic region.

In both of these procedures the physician has to make an estimate of the length of the stenotic region which is to be dilated or into which a stent is to be deployed in order to assess the length of the balloon to be used for the dilatation or the length of the stent to be deployed. Heretofore, it has been suggested to provide a variety of markers on the distal portion of the guidewire and/or catheters in order to make the length determination of stenosis. Many of these prior efforts involve providing various spacings between multiple radiopaque markers on the distal portion of the guidewire to allow the physician to make the length determination fluoroscopically with the guidewire in position within the artery and the markers traversing the stenotic region. However, due to the two dimensional nature of the fluoroscopy, these prior methods have not always been very accurate because of the orientation of the stenosis and the guidewire within the stenosis is not always suitable for an accurate length determination.

SUMMARY OF THE INVENTION

The invention is generally directed to an improved method and devices for the measuring of a distances within a patient's body lumen such as the length of stenosis within a patient's coronary arteries.

The invention involves the use of a guidewire which has at least one marker or other location indicia on the distal portion of the guidewire which is observable (e.g. fluoroscopically) by the physician. The guidewire is positioned within the patient's body with the distal marker being placed at or adjacent to one end of the intracorporeal location to be measured and then the guidewire is repositioned so that the same distal marker is placed at or adjacent to the other end of the intracorporeal location. The portion of the guidewire which extends out of the patient's body moves the same distance as the distal marker is moved between the ends of the intracorporeal location to be measured and measurement of the extracorporeal movement of the guidewire is determined in order to determine the length of the intracorporeal location.

The movement of the proximal portion of the guidewire which extends out of the patient can be measured in a variety of ways. For example, ruler-like indicia, which can be seen and/or felt, e.g. transverse ridges or grooves, can be placed on the surface of the proximal extremity of the guidewire which extends out of the patient. To make the internal measurement, the guidewire is located within the patient's body so that the distal marker on the guidewire is positioned at or adjacent to one end of the intracorporeal location to be measured. The first external position of an indicia on the proximal end of the guidewire is then referenced with respect to an external reference point, e.g. the proximal end of the guiding catheter adapter. When the guidewire is moved to position the distal marker at the other end of the intracorporeal location, the indicia on the proximal end of the guidewire likewise moves, and the distance it moves is the intracorporeal distance measured. The physician or other operator can determine the distance within the two intracorporeal locations by visual or manual reference to the relative movement of the ruler-like indicia to the external point of reference.

Other methods can be used to determine the distance traveled by the guidewire when changing the location of the distal marker. A wheeled distance sensing member may be pressed into engagement with the surface of the proximal end of the guidewire extending out the patient. The wheel of the distance sensing member rotates as the guidewire is moved and this rotation can be converted into a suitable distance readout. Similarly, an electro-optical system may be utilized to measure the distance the guidewire moves. A wide variety of other methods may be employed to make the distance measurement. These distance measuring systems must be referenced to a suitable substrate, e.g. the adapter on the proximal end of the guiding catheter, so that the axial movement of the guidewire can be properly detected. To ensure that the distal position of the guidewire is not lost, it is preferred to first position the distal marker on the guidewire at the proximal intracorporeal location and then advance the guidewire distally within the body lumen until the distal marker is adjacent to the distal intracorporeal location. The reverse procedure can be employed, i.e. place the distal marker at the distal end of the stenosis first and then at the proximal end of the stenosis, but in this case the guidewire must then traverse the lesion again which can be time consuming. However, by first placing the distal marker at the most distal end of the lesion and then withdrawing the guidewire proximally to move the distal marker to the proximal end of the lesion ensures that any slack present in the guidewire will be removed and thereby ensure an accurate measurement.

The present invention provides an improved method and devices for measuring the distance between two locations within a patient's body, particularly a lesion within a blood vessel. These and other advantages of the invention will become more apparent from the following detailed description of the invention when taken in conjunction with the accompanying exemplary drawings.

BRIEF DESCRIPTION OF THE DRAWINGS

FIG. 5A is an elevational view of a guidewire within a patient's blood vessel with the distal marker adjacent to the proximal end of an arterial stenosis.

FIG. 5B is an elevational view similar to that of FIG. 5A except that the distal marker is adjacent to the distal end of an arterial stenosis.

DETAILED DESCRIPTION OF THE INVENTION

Figure 1:
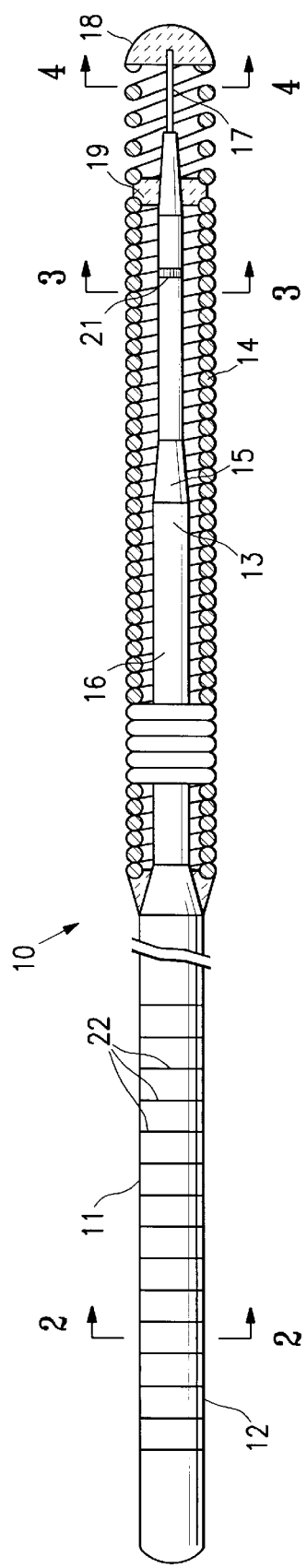
FIG. 1 is a schematic, elevational view, partially in section, of a guidewire embodying features of the invention.
Figure 4:
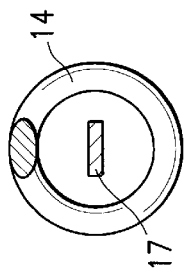
FIG. 4 is a transverse cross sectional view of the guidewire of FIG. 1 taken along lines 4—4.
Figure 3:
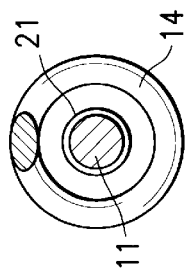
FIG. 3 is a transverse cross sectional view of the guidewire system of FIG. 1 taken along lines 3—3.
Figure 2:
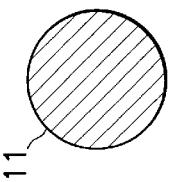
FIG. 2 is a transverse cross sectional view of the guidewire of FIG. 1 taken along lines 2—2.

FIGS. 1–4 illustrate an intracorporeal guidewire 10 embodying features of the invention which generally includes an elongated core member 11 with an elongated proximal shaft section 12 and a tapered distal shaft section 13 and a helical coil 14 disposed about and secured to the tapered distal shaft section 13. The tapered distal shaft section 13 may have one or more tapered portions 15 and one or more constant diameter portions 16. A flat shaping ribbon 17 extends to the rounded plug 18 which is formed when the distal end of the coil 14 is welded to the distal end of the flat shaping ribbon 17. The coil 14 is also joined to the distal shaft section 13 at an intermediate location 19 and at its proximal end 20, usually by soldering or brazing. A distal radiopaque marker 21 is secured to the constant diameter portion 16 proximal to the shaping ribbon 17 so that the ribbon can be shaped without displacing the marker 21. Preferably, the marker 21 is positioned as close as possible to the intermediate location 19 so that the guidewire 10 need not be disposed too far distally when positioned adjacent to the distal end of lesion to be dilated to measure the length of the lesion.

The proximal extremity of the proximal shaft 12 is provided with ruler-like indicia 22, such as ridges or grooves, to allow the physician or other operator to visually or manually detect how far the guidewire is axially moved with respect to a reference point such as the proximal end of an adapter 23 on the proximal end of a guiding catheter (not shown) when the distal marker on the guidewire is moved from the first to the second intracorporeal location. The spacing between the indicia should be of a standard length unit so that the physician can convert the number of indicia to a length measurement. The indicia may have suitable numbers adjacent to the indicia providing the unit measurement, e.g. mm or inches as shown.

FIGS. 5A and 5B illustrate the measuring the length of a lesion 30 within a patient's blood vessel 31 by means of the guidewire 10 shown in FIGS. 1–4. In FIG. 5A the guidewire 10 is shown as being positioned within the blood vessel 31 so that the radiopaque marker 21 is adjacent to the proximal end 32 of the lesion 30. In FIG. 5B the position of the guidewire 10 has been changed so that the radiopaque marker 21 is adjacent to the distal end 33 of the lesion 30. The distance "$L_1$" between the proximal and distal ends 32 and 33 of lesion 30 can be determined by subtracting the distance "$L_2$" from the distance "$L_3$" shown at the proximal portion of the core 11 which extends out of the patient.

Figure 6A:
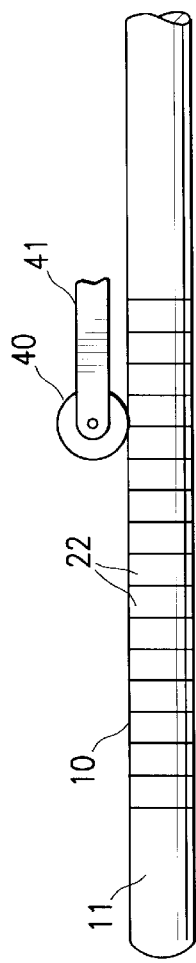
FIG. 6A is a schematic representation of a wheeled distance measuring device in position when the distal marker on the guidewire is located at or adjacent to the proximal end of the arterial stenosis.
Figure 6B:
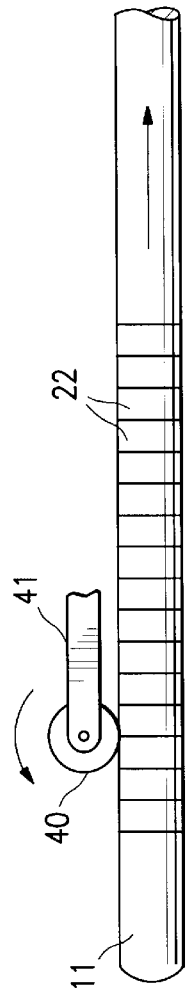
FIG. 6B is a schematic representation of the wheeled distance measuring device shown in FIG. 6A when the distal marker on the guidewire is located at or adjacent to the distal end of the lesion.

FIGS. 6A and 6B illustrate a method and system for detecting the guidewire movement utilizing a wheeled distance measuring device 40. The measuring device 40 is fixed with respect to a reference point, e.g. the adapter on the proximal end of a guiding catheter (not shown) by means of a yoke 41. In FIG. 6A the distal marker 21 is located at or adjacent to the proximal end of the lesion and in FIG. 6B the distal marker 21 is located at or adjacent to the distal end of the lesion.

Figure 7:
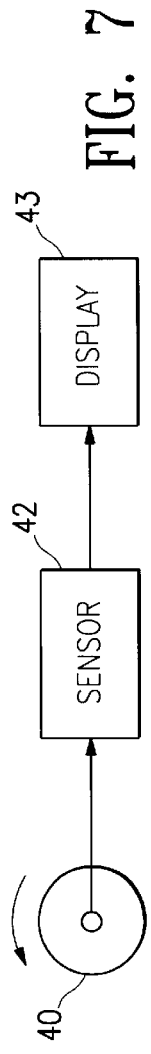
FIG. 7 illustrates sensor and display units for wheeled distance measuring devices such as shown in FIGS. 6A and B.

FIG. 7 illustrates a method and system for measuring the length of a lesion or other intracorporeal location within a patient's body by means of a wheeled distance measuring device 40 as shown in FIGS. 6A–B. In this system a wheel 40 is pressed against the surface of the proximal extremity of the core member 11. The wheel 40 rotates when the guidewire 10 is moved to locate the radiopaque marker 21 at the ends 32 and 33 of the lesion 30. This rotational movement of the wheel 40 is related to the distance the guidewire moves and the rotational movement is sensed by sensor 42 which generates a signal representing the distance measured. The distance signal is transmitted to the display unit 43 as the distance measured by the radiopaque marker 21.

Figure 8:
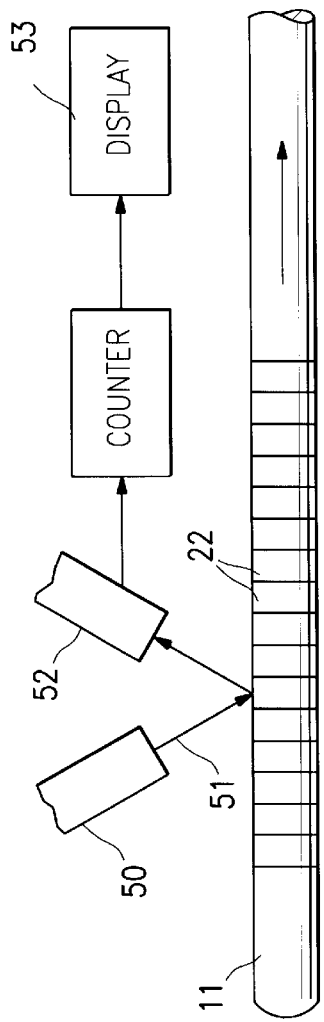
FIG. 8 is an elevational view of an electro-optical system for measuring the distance the guidewire moves when measuring the distance between the first and second intracorporeal locations.

FIG. 8 illustrates another method and system for measuring the length of a lesion or other intracorporeal location within a patient's body. In this system, the proximal extremity of the core member 11 is provided with a series of equally spaced surface disruptions such as ridges or grooves or indicia 22. A laser or other light source 50 is positioned to emit a light beam 51 onto the surface of the core member 11 as shown. A sensor unit 52 receives light reflected from the surface of core member 11 and generates a signal representing the received reflected light. When the guidewire 10 is moved to position the distal marker 21 adjacent to the ends 32 and 33 of the lesion 30, the light reflected from the surface of the proximal extremity of the core member 11 will be disturbed by the equally spaced disruptions or indicia 22 on the core member 11 which will cause a change in the output signal of the sensor unit 52. The output signal changes can be detected as a series of peaks or valleys which can be counted and displayed on the display unit 53 as a distance.

Figure 9A:
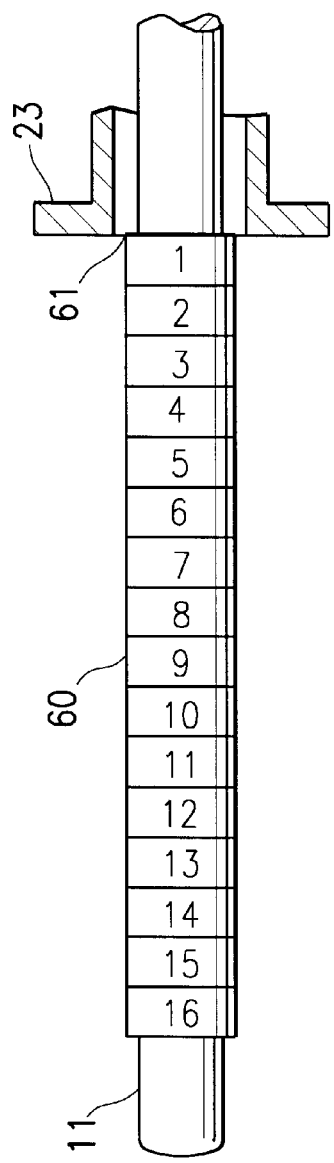
FIGS. 9A and 9B are elevational views of an alternative system for measuring the distance between the first and second intracorporeal locations wherein a slidable sheath is provided on the core of the guidewire having indicia for measuring guidewire movement.
Figure 9B:
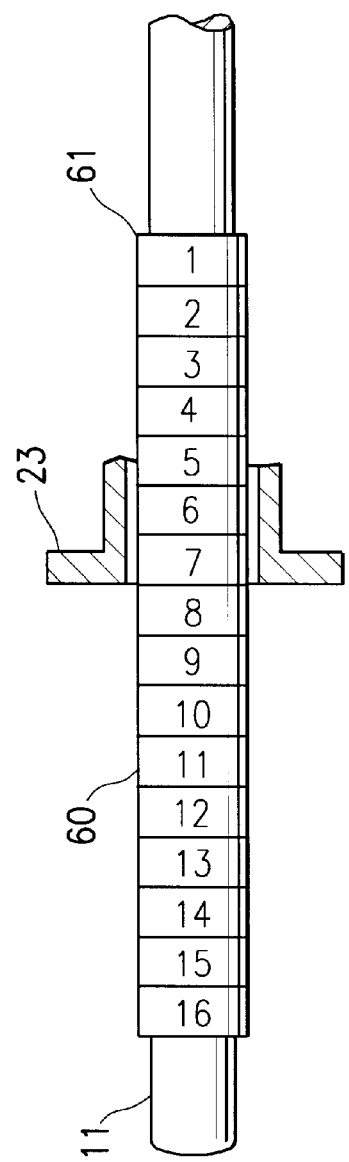

Another method and system for measuring the distance is shown in FIGS. 9A and 9B. In this system a slidable sleeve or other member 60 is mounted on the exterior of the proximal portion of the core member 11 which extends out of the patient. The sleeve 60 is preferably mounted to the proximal portion of the core member 11 so as to be slidable but to fit tightly enough to prevent inadvertent relative movement. When the distal marker (not shown) on the guidewire 10 is placed at or adjacent to the proximal end 32 of the lesion 30, the position of the sleeve 60 on the core member 11 is slidably adjusted until the distal end 61 of the sleeve 60 is adjacent to the proximal end of the adapter 23 on the proximal end of the guiding catheter (not shown). This locates the base measurement on the sleeve which in this case is at zero. When the position of the guidewire 10 is moved distally to shift the distal marker (not shown) to the distal end of the lesion, the sleeve 60 moves with the guidewire into the proximal opening of the adapter 23. The distance moved can be read off the indicia on sleeve 60 adjacent to the proximal end of the adapter 23.

The indicia on the proximal extremities of the guidewire generally will extend a distance of about 3 to about 40 cm to allow for the measurements of lesions throughout the patient's coronary arterial system. With a conventional guidewire of about 175 cm, it is preferred that the markings on the proximal extremity of the core member start at a location about 40 to about 85 cm from the proximal end of the guidewire to ensure that the markings are properly located for measuring the intracorporeal length. With the use of a sheath or other slidable member such as shown in FIGS. 9A and 9B, the indicia need extend only the maximum length of the longest lesion or other intracorporeal location expected to be measured.

A wide variety of other means well know to those skilled in the art may be employed to detect the guidewire movement which can then be translated to the measurement of a length of a region within a patient's body.

It will be apparent from the foregoing that, while particular forms of the invention have been illustrated and described, various modifications can be made without departing from the spirit and scope of the invention. Moreover, those skilled in the art will recognize that features shown in one embodiment may be utilized in other embodiments.

What is claimed is:

1. A guidewire for performing an intraluminal procedure, comprising:
   an elongated core having a proximal section with a proximal portion configured to extend out of the patient during an intraluminal procedure and a distally tapered distal section;
   a. a flexible body disposed about the distal section of the elongated core;
   b. a radiopaque marker on a distal part of the guidewire spaced proximal to the distal end of the core member; and
   c. a plurality of longitudinally spaced indicia disposed on a proximal portion of the proximal section configured to extend out of the patient during the intraluminal procedure, one of said indicia located so as to represent a base location for the marker on the distal part of the guidewire.

2. The guidewire of claim 1 wherein there are at least about 3 indicia on the proximal portion of the proximal section.

3. The guidewire of claim 1 wherein the plurality of indicia are uniformly spaced.

4. The guidewire of claim 1 wherein the indicia are spaced at least about 3 mm apart.

5. The guidewire of claim 1 wherein the indicia are spaced at about 0.5 to about 3 mm.

6. The guidewire of claim 1 wherein the most proximal indicia on the proximal extremity of the core member extends at least about 40 cm from the proximal end of the core member.

7. The guidewire of claim 1 wherein the marker on the distal section of the guidewire is spaced at least about 3 cm from the distal end of the guidewire.

8. A guidewire for performing an intraluminal procedure, comprising:
   an elongated core having a proximal section with a proximal portion configured to extend out of the patient during an intraluminal procedure and
   a. a distally tapered distal section;
   b. a flexible body disposed about the distal section of the elongated core;
   c. a radiopaque marker on a distal part of the guidewire;
   d. at least one indicia disposed on a proximal portion of the proximal section configured to extend out of the patient during the intraluminal procedure, said indicia being at a first location so as to represent a first location for the distal radiopaque marker; and
   f. means to determine the distance from the indicia representing the first location for the distal marker to a second location on the proximal core section which represents a second location of the distal marker.

9. A method of measuring a length within a body lumen, comprising:
   a. disposing within a body lumen a guidewire having a distal marker on a distal portion of the guidewire and at least one indicia on a proximal portion of the guidewire which is configured to extend out of the patient during a procedure;
   b. positioning the guidewire within the body lumen so that the distal marker is adjacent to one end of the length to be measured within the body lumen;
   c. noting the first position of the proximal marker with respect to a reference point;
   d. moving the guidewire within the body lumen so that the distal marker is adjacent to another end of the length to be measured within the body lumen;
   e. noting the second position of the proximal marker with respect to the reference point; and
   f. determining the distance between the first and second positions of the proximal marker which corresponds to the distance of the length within the body lumen.

10. The method of claim 9 wherein the distal marker of the guidewire is first placed at the proximal end of the length to be measured within the body lumen and then repositioned to the distal end of the length within the body.

11. The method of claim 9 wherein the distal marker of the guidewire is first placed at the distal end of the length to be measured within the body lumen and then repositioned to the proximal end of the length within the body.

12. A method of measuring a length within a body lumen, comprising:
   a. disposing within a body lumen a guidewire having a distal marker on a distal portion of the guidewire and at least one indicia on a proximal portion of the guidewire which is configured to extend out of the patient during a procedure;
   b. positioning the guidewire within the body lumen so that the distal marker is adjacent to one end of the length to be measured within the body lumen;
   c. noting a position of one indicia on the proximal portion of the guidewire with respect to a reference point;
   d. moving the guidewire within the body lumen so that the distal marker is adjacent to another end of the length to be measured within the body lumen;
   e. noting a position of a second indicia on the proximal marker with respect to the reference point; and
   f. determining the distance between the first and second indicia on the proximal portion of the guidewire which corresponds to the distance of the length to be measured within the body lumen.

13. A guidewire system for performing an intraluminal procedure, comprising:
   a. a guidewire including
      i. an elongated core having a proximal section with a proximal portion configured to extend out of the patient during an intraluminal procedure and a distally tapered distal section,
      ii. a flexible body disposed about the distal section of the elongated core,
      iii. a marker on a distal part of the guidewire, and
      iv. a proximal portion of the proximal section configured to extend out of the patient during the intraluminal procedure; and
   b. a device in a positional relationship with respect to a proximal portion of the guidewire extending out of the patient during the procedure for measuring the distance the proximal portion of the guidewire moves during the procedure when the marker on the distal part of the guidewire is moved from one end of an intracorporeal length to be measured to another end of the intracorporeal length.

14. The system of claim 13 wherein the distal marker is spaced proximal to the distal end of the core member.

15. The system of claim 13 wherein the device for measuring the distance moved by the proximal portion of the guidewire is a wheeled measuring devices.

16. The system of claim 13 wherein the proximal portion of the guidewire which extends out of the patient during the procedure is provided with a plurality of indicia and the device for measuring the distance moved by the proximal portion of the guidewire is an optical based measuring system.

17. The system of claim 13 wherein the optical based measuring system includes a light source directed to the surface of the proximal portion of the guidewire extending out of the patient and a light sensor which receives light reflected from the surface of the proximal guidewire portion.

18. A The system of claim 14 wherein the measuring device includes a device for detecting the effect of light reflected from the indicia on the surface of the proximal portion extending out of the patient as the proximal portion moves when the marker on the distal portion of the guidewire is moved from one end of the intracorporeal location to another end of the intracorporeal location.

19. The system of claim 14 including a device for displaying the number of indicia detected by the light sensor.

20. A guidewire for performing an intraluminal procedure, comprising:
   a. an elongated core having a proximal section with a proximal portion configured to extend out of the patient during an intraluminal procedure and a distally tapered distal section;
   b. a flexible body disposed about the distal section of the elongated core;
   c. a radiopaque marker on a distal part of the guidewire; and
   d. an arcuate member slidably mounted on the proximal portion of the proximal section of the core having a plurality of indicia disposed thereon, the position of said arcuate member on the proximal portion being adjustable to a first location relative to a reference point to represent a first end of an intracorporeal length to be measured when the distal marker is adjacent to the first end; and moving with the proximal portion of the core member when the guidewire is moved so that the distal marker is adjacent to a second end of the intracorporeal length to determine the distance from the indicia representing the first location for the distal marker to a second location on the arcuate member which represents a second location of the distal marker so as to thereby determine the distance between the two end of the intracorporeal length.

21. The guidewire of claim 20 wherein the arcuate member is a sheath mounted about the proximal portion of the core member.

22. A method of measuring a length within a body lumen, comprising:
   a. disposing within a body lumen a guidewire having a distal marker on a distal portion of the guidewire and having an arcuate member slidably mounted on a proximal portion of the guidewire which is configured to extend out of the patient during a procedure;
   b. positioning the guidewire within the body lumen so that the distal marker is adjacent to one end of the length to be measured within the body lumen;
   c. longitudinally moving the arcuate member on the proximal portion of the guidewire to align a first indicia with respect to a reference point
   d. moving the guidewire within the body lumen so that the distal marker is adjacent to another end of the length to be measured within the body lumen, with the arcuate member on the proximal portion moving therewith when the guidewire is moved;
   e. noting a position of a second indicia on the arcuate member aligned with respect to the reference point; and
   f. determining the distance between the positions of the first and second indicia on the arcuate member which corresponds to the distance of the length to be measured within the body lumen.

* * * * *

UNITED STATES PATENT AND TRADEMARK OFFICE
CERTIFICATE OF CORRECTION

| | |
|---|---|
| PATENT NO. | : 6,428,512 B1 |
| APPLICATION NO. | : 09/686143 |
| DATED | : August 6, 2002 |
| INVENTOR(S) | : David M. Anderson et al. |

Page 1 of 1

It is certified that error appears in the above-identified patent and that said Letters Patent is hereby corrected as shown below:

Column 7, line 63, claim 17, change "13", to read --16--.

Column 8, line 1, claim 18, change "14", to read --17--.

Column 8, line 8, claim 19, change "14", to read --17--.

Signed and Sealed this

Nineteenth Day of February, 2008

JON W. DUDAS
*Director of the United States Patent and Trademark Office*